United States Patent [19]

Carvajal et al.

[11] Patent Number: 5,390,551
[45] Date of Patent: Feb. 21, 1995

[54] METHOD AND APPARATUS FOR THE ANALYSIS OF GAS IN A MEDIUM, ESPECIALLY HYDROCARBONS

[75] Inventors: Nelson Carvajal, Los Teques; Beatriz Silva; Alejandro Gonzáles, both of Caracas, all of Venezuela

[73] Assignee: Intevep, S.A., Caracas, Venezuela

[21] Appl. No.: 188,837

[22] Filed: Jan. 31, 1994

Related U.S. Application Data

[62] Division of Ser. No. 48,127, Apr. 14, 1993.

[51] Int. Cl.$^6$ .......................... G01N 7/00; G01N 1/24
[52] U.S. Cl. .................................. 73/863; 73/864.35; 73/19.01; 73/19.1; 73/23.38; 73/23.41; 436/139; 436/143
[58] Field of Search .................. 73/23.38, 23.41, 23.42, 73/863.84, 864.35, 864.81, 864.83, 864.84, 864.85, 864.86, 864.87, 863, 19.01, 19.1; 436/29, 139, 143

[56] References Cited

U.S. PATENT DOCUMENTS

| | | | |
|---|---|---|---|
| 2,534,489 | 12/1950 | Webber et al. | 73/864.35 |
| 3,357,232 | 12/1967 | Lauer | 73/864.81 |
| 3,715,910 | 2/1973 | Fore et al. | 73/23.41 |
| 3,753,656 | 8/1973 | Matson et al. | 436/139 |
| 3,790,348 | 2/1974 | Bossart et al. | 73/23.38 |
| 3,888,109 | 6/1975 | Sharki et al. | 73/23.2 |
| 3,927,978 | 12/1975 | Wasik | 426/143 |
| 4,096,734 | 6/1978 | Khayat | 73/23.41 |
| 4,101,282 | 7/1978 | Ririe | 73/864.35 |
| 5,222,032 | 6/1993 | Fleming | 73/19.1 |
| 5,235,843 | 8/1993 | Longhorst | 73/19.1 |
| 5,266,496 | 11/1993 | Dacruz | 73/23.41 |
| 5,277,074 | 1/1994 | Poole et al. | 73/864.35 |

FOREIGN PATENT DOCUMENTS

| | | | |
|---|---|---|---|
| 705303 | 12/1979 | U.S.S.R. | 73/19.01 |
| 739362 | 6/1980 | U.S.S.R. | 73/864.81 |
| 983515 | 12/1982 | U.S.S.R. | 73/19.01 |

OTHER PUBLICATIONS

Kriegel, Monroe, W., "Analysis For Hydrocarbons in the Presence of Nitrous Oxide", pp. 447–462, Mar. 1944.

*Primary Examiner*—Hezron E. Williams
*Assistant Examiner*—Daniel S. Larkin
*Attorney, Agent, or Firm*—Bachman & LaPointe

[57] ABSTRACT

A method for determining the concentration of a monitored gas in the head space of a confined space containing a medium material at a given temperature ($T_1$), includes the steps of: (a) providing an extracting apparatus having a chamber for receiving a sample volume of the material to be extracted from the confined space; (b) controlling the temperature of the chamber such that the temperature of the chamber is maintained at the given temperature ($T_1$) of the confined space; (c) withdrawing a sample volume of the material from the confined space and into the chamber; (d) feeding a volume of inert gas into the chamber and mixing the inert gas with the material to form a mixture; (e) allowing the mixture to reach equilibrium wherein a head space of gas is formed in the chamber over the material; (f) withdrawing a first gas sample from the head space of the chamber; (g) determining the concentration of the monitored gas in the first gas sample; (h) expelling the gas from the head space of the chamber; (i) repeating steps (d)–(g) so as to determine the concentration of the monitored gas in at least a second gas sample; (j) determining the equilibrium constant of the material at the given temperature ($T_1$) in accordance with a specified formula; and (k) determining the concentration of the monitored gas in the head space of the confined space in accordance with another specified formula.

7 Claims, 4 Drawing Sheets

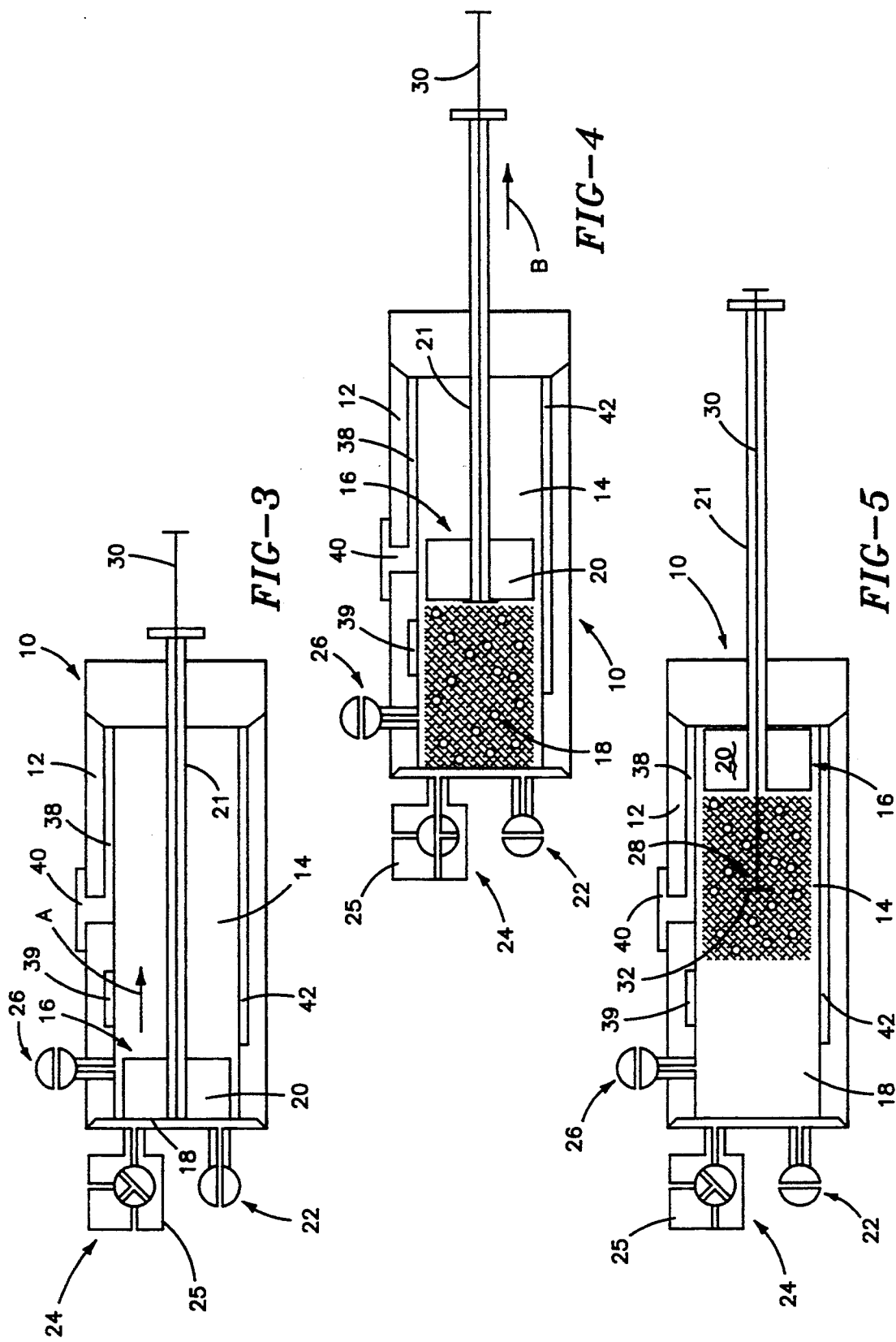

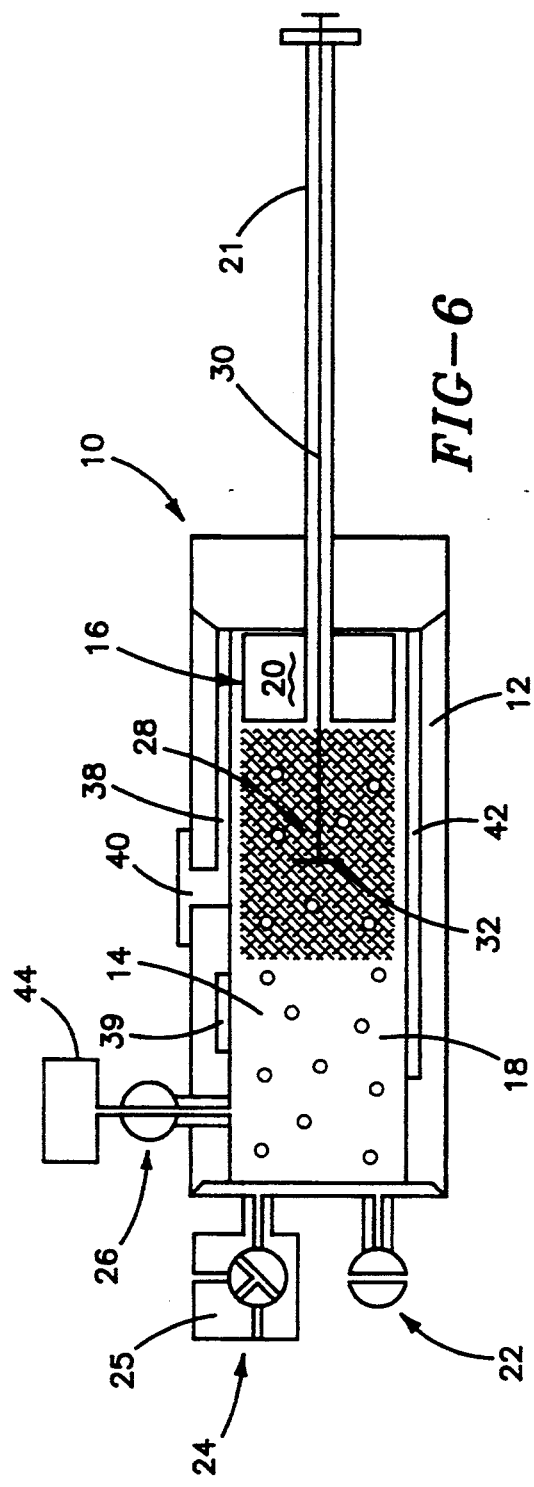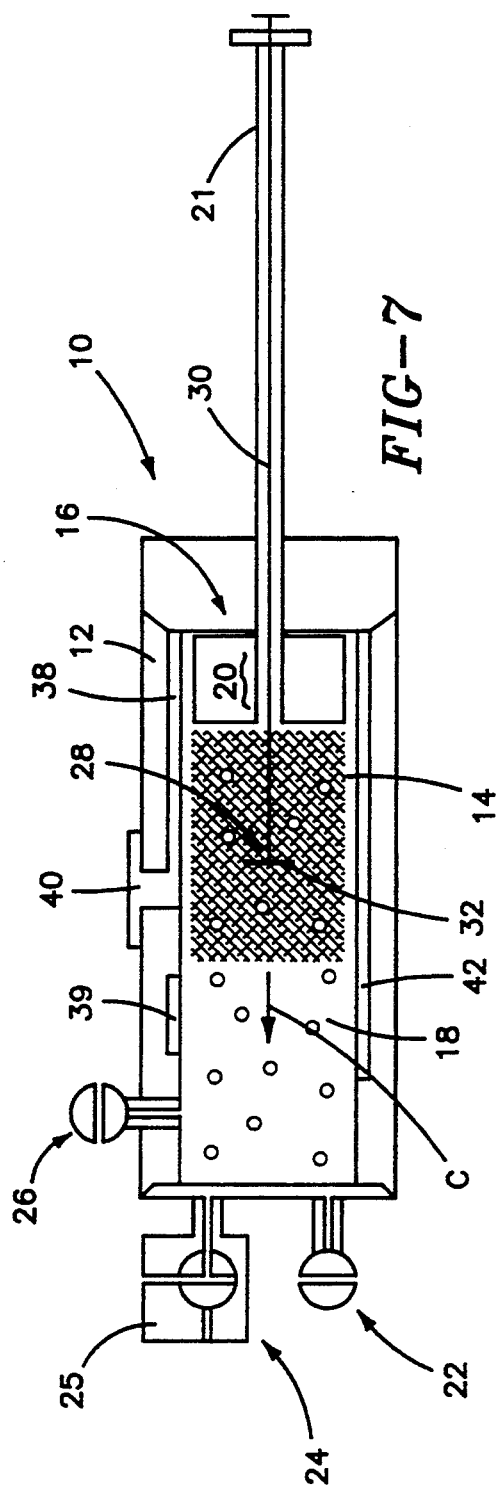

DETERMINATION OF K FOR 75°C AND 63.5°C

METHOD AND APPARATUS FOR THE ANALYSIS OF GAS IN A MEDIUM, ESPECIALLY HYDROCARBONS

This is a division of application Ser. No. 08/048,127 filed Apr. 14, 1993.

BACKGROUND OF THE INVENTION

The present invention relates to a method and apparatus for determining the concentration of a monitored gas in a medium in a storage vessel and, more particularly, the concentration of hydrogen sulfide gas in storage facilities for storing hydrocarbon products including petroleum products.

Hydrogen sulfide gas is a colorless, naturally occurring gas which is co-produced with many of the world's crude oils. Hydrogen sulfide gas is a particularly deadly gas. It has been found that concentrations of hydrogen sulfide gas of above 320 ppm have led to unconsciousness and even death. Oil companies, utilities and the like must contend with the problem of hydrogen sulfide gas which results in storage facilities where crude oils are held. The deadly gas collects in the vapor spaces or head spaces of oil tankers, barges, trucks, storage tanks, rail cars and the like. The release of hydrogen sulfide gas can become a dangerous problem during the transportation and storage of petroleum products as the concentration of the hydrogen sulfide gas can increase significantly under certain conditions. For example, research has shown that hydrogen sulfide concentrations increase in fuel oils due to the fact that the oils must be stored and transported at relatively high temperatures, that is, at temperatures of between about 120° F. to about 180° F. During the transportation of the oil the cargo tends to be agitated which further increases the likelihood of the release of gas during transport. It has been found that for every increase in temperature of about 40° F. to 45° F. in the residual oil during storage and/or transport, the concentration of the H₂S gas released may be doubled.

There is a growing awareness of the environmental concerns involved with emissions of H₂S gas. As a result, product specifications are subject to close scrutiny. It is imperative that the supplier of petroleum products as well as the purchaser of same be able to determine with accuracy the concentration of the poisonous H₂S gas in the product being bought and sold. While there are readily available mechanisms for analyzing the concentration of H₂S gas in a particular medium at one point in time, there has yet to be developed a system for predicting the levels of hydrogen sulfide gas in a product after transportation and storage at a given temperature.

Naturally, it would be highly desirable to provide a system and method for determining the concentration of a monitored gas in a medium and particularly hydrogen sulfide in petroleum products and to be able to predict the levels of hydrogen sulfide in a petroleum product under varying temperature conditions.

Accordingly, it is the principal object of the present invention to provide a method for determining the maximum concentration of a monitored gas in the head space of a confined space containing a medium such as a hydrocarbon medium or other media at a given temperature.

It is a further object of the present invention to provide a method as aforesaid wherein the equilibrium constant between the liquid phase and the gas phase of a medium contained in a confined space can be determined for any temperature.

It is a still further object of the present invention to provide a method as aforesaid wherein the actual concentration of the monitored gas can be determined at any temperature.

It is a particular object of the present invention to provide a system for carrying out the methods as aforesaid which is readily usable in the field.

It is another object of the present invention to provide an apparatus for extracting samples of a medium from a storage vessel and maintaining the samples under controlled temperature conditions for later analysis at that temperature.

Further objects and advantages of the present invention will appear hereinbelow.

SUMMARY OF THE INVENTION

In accordance with the present invention the foregoing objects and advantages are readily obtained.

The present inventions relates to a method and apparatus for determining the concentration of a monitored gas in a medium in a storage vessel and, more particularly, a method and apparatus for determining the concentration of hydrogen sulfide gas in hydrocarbon products stored and transported in confined spaces. The method for determining the concentration of the monitored gas in the head space of a confined space containing a medium such as a petroleum product at a given temperature comprises withdrawing a sample of the medium from the confined space or storage vessel under controlled conditions so as to maintain the temperature of the sample at a desired temperature. The sample of medium of known volume is thereafter mixed with a known volume of inert gas in a chamber under controlled temperature conditions. The mixture is allowed to reach equilibrium wherein a head space of a gas is formed over the sample medium in the chamber. A sample of the gas is thereafter withdrawn and the concentration of the monitored gas in the gas sample is determined. After expelling the remainder of the gas from the head space, a further known volume of inert gas is introduced, mixed, allowed to reach equilibrium and another gas sample is withdrawn. From the two samples, an equilibrium constant of the gas and liquid phases of the medium at the controlled temperature is determined. Thereafter, the maximum possible concentration of the monitored gas in the head space of the confined space may be determined in accordance with the following formula:

$$C_{Gmax} = C_{g1} \cdot (K_{T1} + V_g/V_l) \cdot D_f$$

where:
- $C_{g1}$ is the concentration of the monitored gas in the first sample;
- $K_{T1}$ is the equilibrium constant of the medium at temperature $T_1$;
- $V_g$ is the volume of the gas phase in the chamber;
- $V_l$ is the volume of the liquid phase in the chamber; and
- $D_f$ is a dilution factor defined as follows:

$$D_f = \frac{V_g \cdot Wt_t}{Wt_s \cdot V_{vs}}$$

wherein:

$V_g$ is the volume of inert gas in liters;

$Wt_s$ is the weight of the sample volume ($V_l$) of the material, in grams;

$Wt_t$ is the total weight of the medium material in grams; and $V_{vs}$ is the volume of the head space of the confined space in liters.

In accordance with a further feature of the present invention, the equilibrium constant of the medium can be determined at any given temperature by repeating the method outlined above to obtain an equilibrium constant $K_{T2}$ at a different control temperature $T_2$. The relationship between lnk and 1/T is substantially linear, so that once equilibrium constants are determined from two temperatures, $T_1$ and $T_2$, a graph of the values is prepared from which the equilibrium constant ($K_{Ta}$) for any temperature ($T_a$) can be determined. Once the equilibrium constant for the medium is determined for a given temperature, the actual concentration of the monitored gas can then be predicted at that temperature with a high degree of accuracy.

In order to carry out the method as aforesaid, an apparatus is employed for withdrawing a sample of the medium from the confined space, mixing the medium with the inert gas and delivering a portion of the inert gas containing the monitored gas for analysis. In accordance with the present invention, the apparatus comprises a housing defining a chamber. A movable partition is mounted in the chamber for defining a variable volume space in the chamber. A drive in the form of piston rod is associated with the partition for moving the partition selectively to increase and decrease the volume of the variable volume space defined within the chamber. A suitable valve mechanism is associated with the variable volume space for selectively feeding the sample of the medium and inert gas into the variable volume space upon actuation of the piston rod for increasing the volume of the variable volume space. A heater is provided on the housing for controlling the temperature of the medium and inert gas in the variable volume space. A stirrer is provided within the variable volume space for mixing the sample of the medium and inert gas and an outlet is provided for withdrawing a portion of the inert gas from the variable volume space for analysis once the mixture reaches equilibrium.

In accordance with a further feature of the present invention the apparatus is readily transportable between the storage vessel containing the medium and an analytical installation for evaluating the concentration of the monitored gas.

The method and apparatus of the present invention not only allow for the determination of the concentration of a monitored gas such as hydrogen sulfide in a medium such as a petroleum product, residual fuel or the like, but further provides a mechanism for predicting the concentration of hydrogen sulfide gas in the head space over the medium under any temperature conditions. Thus, the supplier of a petroleum product can specify to a purchaser with a high degree of accuracy the maximum concentration of hydrogen sulfide to be found in the head space of a storage vessel, ship or the like containing the petroleum product, at any temperature.

It should be appreciated that the method and apparatus may be used for monitoring any gas in a number of different media including, but not limited to, petrochemical products, environmental pollutants, and food additives, and that the gas monitored may be any gas of interest. Further, the media itself could, of course, be any kind of fluid, be it liquid or gas, or solid. Examples of suitable gas detection apparatus include Houston Atlas Lead Acetate tape, for sulfur species; Sievers Chemiluminescence, for sulfur species; Length of Stain Detectors (Dräger Tube), for sulfur species; Antek Chemiluminescence, for nitrogen species; Flame Ionization Detectors (FID), for hydrocarbons and other organic species; Thermal Conductivity Detectors (TCD), for gases in general; Electron Capture Detectors (ECD) for halogenated or highly electronegative species; Helium Ionization Detectors (HID), for permanent gases in general; Flame Photometric Detectors (FPD), for sulfur, and phosphorous species; and any other gas analyzer or gas detector which may be desired.

BRIEF DESCRIPTION OF THE DRAWINGS

A detailed description of the preferred embodiments of the invention follows, with reference to the attached drawings, in which:

FIGS. 3-7 are schematic views of the apparatus of FIG. 1 illustrating various steps of the method according to the invention.

DETAILED DESCRIPTION

Figure 2:
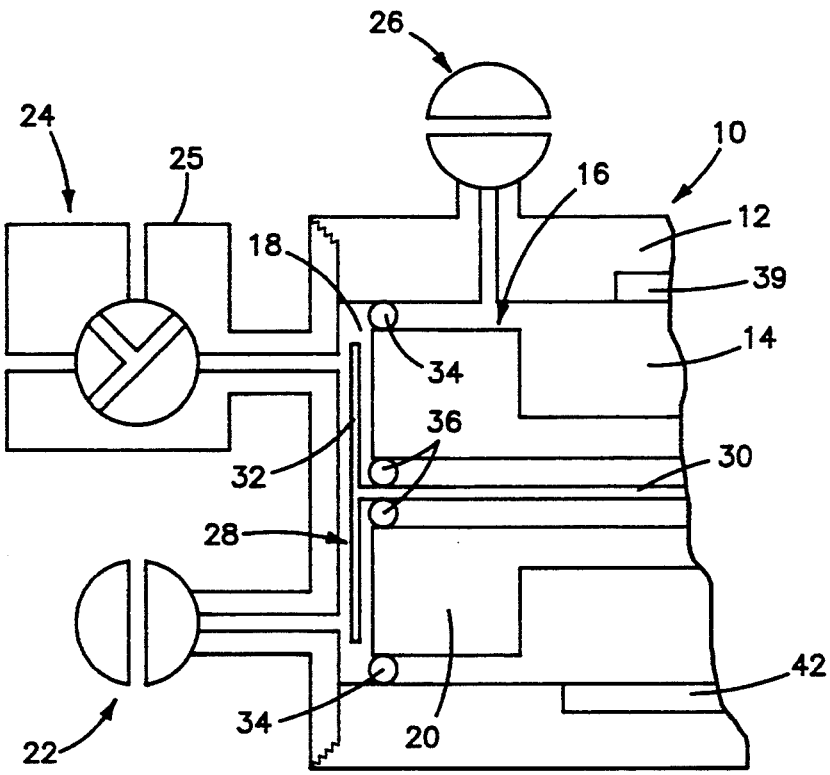
FIG. 2 is an enlarged schematic view of a portion of FIG. 1.

The invention relates to a method and apparatus for determining the concentration of a gas, particularly hydrogen sulfide, in the head space or vapor space of a storage tank for holding a medium such as a hydrocarbon or petroleum product or other media.

As set forth above, such a determination is desirable because the medium in question may contain gases, such as hydrogen sulfide, which are dangerous. The determination of the concentration of such gases in the head space of a storage or transportation tank or any other confined area in which the medium may be stored is the principal object of the present invention.

The actual concentration of a gas in the head space is dependent upon the temperature of the medium. At higher temperatures, larger concentrations of gas are released into the head space from the medium.

According to the invention, the concentration of the gas is determined for any temperature based upon a series of tests conducted on the material at a given temperature. In this manner, a purchaser of the medium can be informed of the expected gas concentration of the gas in question which will be present in a tank or area of a given size at given temperatures. Such a purchaser can then take the necessary precautions to avoid accident or injury from the gas.

According to the invention, a sample of material is obtained from the tank in question. This sample is maintained at a desired temperature, which may preferably be the temperature of the tank, and is tested as follows so as to determine the gas in liquid equilibrium constant K of the medium. The natural log of the equilibrium constant plots as a substantially straight line in inverse relation to temperature. Thus, the constant for any temperature can be determined once the constant is obtained for two temperatures. The total or maximum possible concentration ($C_{Gmax}$) of the monitored gas in the head space is then determined, from which the actual concentration can be predicted at any temperature with an excellent degree of accuracy.

According to the invention, the equilibrium constant is obtained as follows.

The sample of material of known volume is mixed with a known volume of an inert gas in a suitable container. The gas and material are then allowed to return to equilibrium, at which point a head space of gas forms over the material in the container. A first sample of gas is then obtained from the head space of the container and analyzed with a suitable device, depending upon the gas being monitored, so as to determine the concentration of the gas ($C_{g1}$) in this first gas sample.

The head space gas is then ejected from the container, and the material is again mixed with a known volume of inert gas and allowed to return to equilibrium. A head space of gas will again form in the container above the material. A second gas sample is then obtained from the head space and analyzed to determine the concentration of gas ($C_{g2}$) for the second gas sample.

Based upon the phase extraction theory, from which the following formula has been derived, the gas in liquid equilibrium constant (K) for the temperature of the material can be determined from the concentrations ($C_{g1}C_{g2}$) obtained.

$$\ln C_{gn} = \ln C_{g1} \cdot \frac{K + V_g/V_l}{K} + n \cdot \ln \frac{K}{K + V_g/V_l} \quad (1)$$

wherein:
$C_{gn}$ is the gas concentration in gas sample n;
$C_{g1}$ is the gas concentration for a first or known gas sample;
K is the gas in liquid equilibrium constant;
$V_g$ is the volume of gas in the test container;
$V_l$ is the volume of liquid in the test container; and
n is the number of gas samples taken (the number of phase extractions).

The aforedescribed relation provides an excellent estimate of the equilibrium constant for two gas samples or phase extractions. Additional phase extractions are preferably performed if practical, so as to further enhance the accuracy of the constant so obtained.

Equation 1 above is a linear relation, such that, for two given measurements or phase extractions, K can be determined as follows:

$$K = \frac{V_g/V_l \cdot e^x}{1 - e^x}, \quad (2)$$

wherein:

$$x = \frac{\ln C_{gn} - \ln C_{g1}}{n - 1}. \quad (3)$$

The equilibrium constant ($K_{T1}$) so obtained is the equilibrium constant for the temperature $T_1$ of the medium.

As set forth above, the relationship of lnK v. 1/T is substantially linear. Thus once the constant is determined for two temperatures, a plot of the two temperature and equilibrium constant values will provide a straight line from which the constant for any desired temperature can be determined.

Thus, according to the invention, a sample of medium is obtained at a second temperature $T_2$ and tested through phase extraction as above, and a second equilibrium constant $K_{T2}$ is determined. $K_{T1}$, $K_{T2}$, $T_1$, and $T_2$ are then plotted and the linear graph will provide the equilibrium constant $K_{Ta}$ for any temperature $T_a$. According to the invention, the actual gas concentration ($C_{GTa}$) in the head space at any temperature $T_a$ can then be determined, as follows.

From the equilibrium constant and the first phase extraction and measured concentration ($C_{g1}$), the total gas concentration ($C_L°$) in the medium, and the total or maximum possible gas concentration ($C_{Gmax}$) in the head space can be determined.

The total gas concentration in the medium, $C_L°$, is determined as follows:

$$C_L° = C_{g1} \cdot (K_{T1} + V_g/V_l) \quad (4)$$

wherein:
$C_{g1}$ is the gas concentration obtained during the first phase extraction;
$K_{T1}$ is the equilibrium constant at the temperature of the first phase extraction;
$V_g$ is the volume of inert gas; and
$V_l$ is the volume of the sample of medium.

From $C_L°$, the total or maximum possible gas concentration in the head space $C_{Gmax}$ is obtained as follows:

$$C_{Gmax} = C_L° \cdot D_f \quad (5)$$

$D_f$ is a dilution factor obtained as follows:

$$D_f = \frac{V_g(l)}{Wt_s(g)} \times \frac{Wt_T(g)}{V_{vs}(l)}, \text{ wherein} \quad (6)$$

$V_g(l)$ is the volume of inert gas in liters;
$Wt_s(g)$ is the weight of the sample of medium, in grams;
$Wt_T(g)$ is the weight of the total amount of medium stored in the confined space, in grams; and
$V_{vs}(l)$ is the volume of the vapor space or head space, in liters, in the confined space.

Once $C_{Gmax}$ is determined, and $K_{Ta}$ is provided from the aforementioned graph or plot, the actual gas concentration in the head space, $C_{GTa}$, for any given temperature Ta can be determined as follows:

$$C_{GTA} = \frac{C_{Gmax}}{K_{Ta} + V_g/V_l} \quad (7)$$

wherein:
$K_{Ta}$ is the gas in liquid equilibrium constant for temperature $T_a$, determined from the plot of lnK v. 1/T.

As can be seen, the gas concentration $C_{GTa}$ for any temperature ($T_a$) can be predicted based upon the determination of $C_{Gmax}$ and $K_{Ta}$. It therefore becomes a simple matter to predict such concentrations, according to the invention, for any temperature in which the user or purchaser is interested.

It should be noted that the gas concentration of samples, that is, $C_{g1}$, $C_{g2}$, ... $C_{gn}$, can be determined by any of a number of different analysis devices. The device used in the present invention, a Houston Atlas H$_2$S analyzer (Model 825 R-D), measures concentration by providing measurements in terms of area counts ($A_g$)

which are proportional to the actual concentration of monitored gas in the sample. With the Houston Atlas device, the $A_g$ measurement is calibrated with a calibration factor, $R_f$, to provide the actual monitored gas concentration in the sample. $R_f$ is obtained by passing a sample of gas containing a known amount of monitored gas through the device. The device will yield a response in terms of area counts. $R_f$ is a ratio of the known amount of monitored gas to the obtained area count, and is used for that device to calibrate all other measurements taken. Obviously, different devices could require similar calibration factors or other adjustments to provide the actual concentration. The device used, as well as any calibration involved, are not critical and any device which provides the concentration of monitored gas may suitably be used according to the invention. Measurements with a Houston Atlas device, in terms of $A_g$ and calibration with $R_f$, are further illustrated in the Example set forth below.

It should also be apparent from a consideration of formula 4 and 5 that $C_{Gmax}$ could be determined directly from the equilibrium constant, without first determining $C_L°$, according to the following formula:

$$C_{Gmax} = C_{g1} \cdot (K_{T1} + V_g/V_l) \cdot D_f \qquad (8)$$

Referring to the drawings, an apparatus for carrying out the method of the invention, as well as the various steps of the method, will be described and illustrated.

Figure 1:
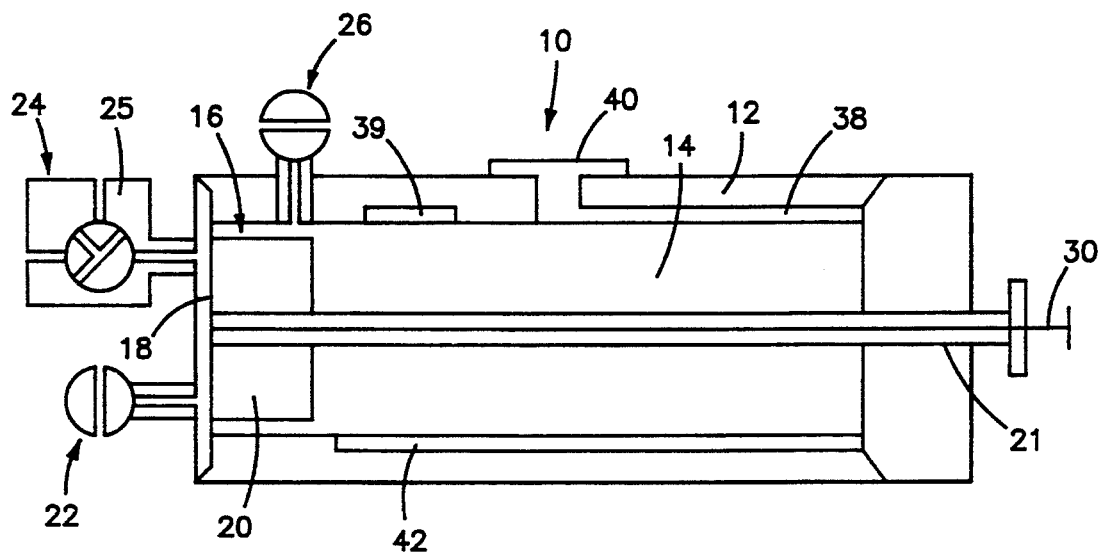
FIG. 1 is a schematic view of an apparatus according to the invention.

FIG. 1 schematically illustrates an apparatus 10 for carrying out the method of the present invention. Apparatus 10 is used to draw a sample volume of medium to be tested from a storage tank or other confined space, and to prepare a head space gas sample from the sample volume of medium which can be analyzed to determine the concentration of a monitored gas, all the while maintaining the sample at controlled temperature conditions.

Apparatus 10 comprises an elongated housing 12 defining a chamber 14. A partition 16 is disposed in chamber 14 so as to define a variable volume space 18 (best shown in FIG. 4) within chamber 14. Partition 16 may preferably be a piston 20 movably disposed in chamber 14.

In the embodiment shown in the drawings, variable volume space 18 is defined in chamber 14 to the left of piston 20. Thus, movement of piston 20 to the right, as shown in FIG. 4, serves to increase the volume of variable volume space 18. Movement of piston 20 to the left serves to reduce the volume of variable volume space 18. Piston 20 is preferably attached to a drive apparatus such as piston rod 21 to provide the desired movement of piston 20. Piston rod 21 may preferably extend from chamber 14 through housing 12. Piston rod 21 may, of course, be operated manually or connected to any suitable conventional motive apparatus.

A valve 22 is preferably provided for communicating with variable volume space 18, and for introducing a sample material into variable volume space 18.

Another valve 24 may also preferably be provided for introducing an inert gas into variable volume space 18, and for extracting a gas phase from variable volume space 18. Valve 24 may preferably be a three way valve mounted in a multiple outlet housing 25 so as to provide several flow positions as will be further described below.

A gas sample valve 26 is also preferably provided for use in withdrawing a gas sample for analysis from variable volume space 18.

An agitator 28 or other suitable mixer or the like is provided in variable volume space 18. FIG. 2 shows an enlarged schematic view of an end of apparatus 10, including agitator 28. Agitator 28 serves to create turbulence within variable volume space 18 and, thereby, to mix the sample material and inert gas together when a sample is being measured as more fully set forth below. Agitator 28 preferably includes a stirring rod 30 disposed in variable volume space 18. Rod 30 may preferably be mounted through a hollow portion of piston rod 21, and may be mounted for at least partially extending through partition 16 into variable volume space 18. An impeller 32 or other stirring device may preferably be disposed on the end of stirring rod 30. Stirring rod 30 is also preferably slidably mounted within piston rod 21 so that, when piston rod 21 is moved to the right to enlarge variable volume space 18, agitator 28 can remain in place, and thereby extend into variable volume space 18 where it can be used to mix the contents of variable volume space 18.

Still referring to FIG. 2, piston 20 may be sealingly disposed against the walls of housing 12 through seal member 34. Further, stirring rod 30 may be sealingly disposed within piston rod 21 through seal member 36. Seal members 34, 36 may be of any known structure or type which provides a sliding and sealing relation between piston 20 and housing 12 on the one hand, and between piston rod 21 and stirring rod 30 on the other.

Returning to FIG. 1, housing 10 may preferably be provided with a temperature control apparatus, which may preferably include a heater 38 and temperature sensors 39 mounted on housing 12, and a visual temperature display 40. Housing 12 also preferably includes insulation 42 for inhibiting heat exchange between housing 12 and the surrounding environment. In this way, control of the temperature of the material in chamber 14 is facilitated. Naturally, any of numerous other conventional means may suitably be employed to obtain and maintain a desired temperature in variable volume space 18.

Apparatus 10 operates, according to the invention, as follows. FIG. 1 shows apparatus 10 ready for use, with piston 20 disposed to the left, so that variable volume space 18 is minimal in size, and with valves 22, 24, and 26 closed.

The temperature of medium to be tested is measured, and the temperature control apparatus of housing 12 is set to provide and maintain this or some other desired temperature in chamber 14, particularly in variable volume space 18 of chamber 14.

Valve 22 is connected to the storage tank or confinement area (not shown) containing the material of interest.

Valve 24 is preferably connected to a source or supply of an inert gas (not shown).

Referring to FIG. 3, valve 22 is opened and piston 20 is drawn partially to the right as indicated by arrows A so as to draw a desired volume of material into variable volume space 18. FIG. 4 shows apparatus 10 with piston 20 disposed partially to the right and with a sample of material containing monitored gas to be tested in variable volume space 18. When piston 20 has reached the desired position, where a desired volume of material has been drawn into variable volume space 18, valve 22 is closed.

Valve 24 is then opened to the source of inert gas, as shown in FIG. 4, and piston 20 is displaced further still to the right as shown by arrow B in FIG. 4, for example to a position as shown in FIG. 5, so as to draw a known volume of inert gas through valve 24 and into variable volume space 18.

Valve 24 is then closed, and stirring rod 30 is displaced to the left as viewed in FIG. 5 to a position where impeller 32 is disposed within variable volume space 18. Impeller 32 is then actuated so as to thoroughly mix the material with the inert gas, and the contents of variable volume space 18 are allowed to return to equilibrium, with a gas phase head space being formed over the material which head space will contain inert gas and monitored gas if any is present. The time necessary to reach sufficient equilibrium depends upon the material being tested. For a typical petroleum product, a time of between about 5 minutes to about 15 minutes may generally be sufficient.

Valve 26 is connected to a suitable gas analyzer 44, shown schematically in FIG. 6. Once equilibrium is reached as above, valve 26 may be opened, as shown, and a sample of gas is drawn off through valve 26 into analyzer 44 where the concentration of monitored gas in the gas sample is measured. This measured value corresponds to $C_{g1}$ as set forth above in the discussion of the method of the present invention.

Also as previously set forth, the method of the present invention relies in part on the multiple head space phase extraction theory and calls for expulsion of the gaseous head space after $C_{g1}$ is obtained, the feed of additional inert gas, and the taking and measurement of additional gas samples. This process is performed at least twice, according to the invention, and preferably three times or more, if practical. That is, at least two and preferably three phase extractions are performed.

Valve 24 may be a three way valve as shown in the drawings, and may have a closed position as shown in FIGS. 1-3, 5 and 6, a position for feed of inert gas as shown in FIG. 4, and a position for discharging the gaseous phase occupying the head space of the variable volume space 18, upon movement of piston 20 to the left as indicated by the arrow C in FIG. 7, to a discharge area (not shown), this position being illustrated in FIG. 7.

At this point, valve 24 may be re-opened to the source of inert gas, as shown in FIG. 4, and the above steps, beginning with the feeding of a volume of inert gas, are repeated to provide a second gas sample measured for a second gas concentration ($C_{g2}$). Phase extractions as above may be conducted so as to provide $C_{g3}$, $C_{g4}$, ... $C_{gn}$ as desired.

In use, apparatus 10 is preferably attached to the storage container and inert gas source to obtain the sample volume of material. Apparatus 10 may then be disconnected and carried to the proper analyzer, where attachment is made through valve 26 to allow gas samples to be measured.

From the measured concentrations, the equilibrium constant, total gas concentration in the medium, total or maximum gas concentration in the head space, and ultimately the actual gas concentration at any temperature can be determined with accuracy as set forth in the aforedescribed method.

The following example further illustrates the method of the present invention.

EXAMPLE

A fuel oil was tested for concentration of hydrogen sulfide. A 3 ml sample volume, ($V_l$), of the fuel oil was obtained and placed in a thermal controlled glass syringe having a total volume of 50 ml. The fuel oil had a density of 1 g/ml.

The glass syringe was maintained at a first analysis temperature ($T_1$) of 65° C. (338K).

43 ml of helium ($V_g$) were added to the flask, mixed with the fuel oil, and then allowed to reach equilibrium in accordance with the present invention. A sample of gas from the vapor space of the flask was taken and measured for hydrogen sulfide concentration with a Houston Atlas H$_2$S analyzer (Model 825 R-D).

The gas phase was then extracted, a new dose of helium added and mixed, and a second sample was taken and measured, followed by a third extraction and measurement. The data obtained is set forth below in Table 1:

TABLE 1

| Area proportional to the Conc. of gas for each sample | | |
|---|---|---|
| Sample #(n) | ($A_{gn}$) (area counts) | Ln($A_{gn}$) |
| 1 | 7.5923 × 10$^9$ | 22.7504 |
| 2 | 6.278 × 10$^8$ | 20.2577 |
| 3 | 5.876 × 10$^7$ | 17.8890 |

The equilibrium constant at $T_1$ ($K_{T1}$) was then determined as follows:

$$K_{T1} = \frac{V_g/V_l \cdot e^x}{1 - e^x},$$

wherein:

$$x = \frac{\ln A_{gn} - \ln A_{g1}}{n - 1}..$$

for n=2, x=−2.4927
$K_{T1}$=1.26.

From the equilibrium constant and the calibrated concentration of the first phase extraction, the total concentration of H$_2$S in the fuel oil, $C_L°$, was determined as follows:

$$C_L° = R_f A_{g1} \cdot (K_{T1} + V_g/V_l).$$

$R_f$, the calibration factor for the analyzer used to calibrate $A_{g1}$ to $C_{g1}$, was determined as follows:

$$R_f = \frac{H_2S \text{ Calibration Standard}}{\text{Area 1 Standard}} = \frac{98 \ \mu mol/mol}{4.1561 \times 10^8 \text{ counts}}$$

$R_f$=2.358×10$^{-7}$ μmol/mol/count.

$C_L°$ was then determined to be 27,319 μmol/mol, which converts to 469.5 μg/g.

The maximum gas concentration $C_{Gmax}$ was then determined as follows:

$$C_{Gmax} = C_L° \cdot D_f,$$

wherein:

$$D_f = \frac{0.043}{3} \times \frac{0.8 \times 10^9}{0.2 \times 10^9} = 0.057$$

$C_{Gmax} = 1,566 \; \mu mol/mol.$

The actual gas concentration at 65° C., $C_{G65°C}$, was then determined as follows:

$$C_{G65°C.} = \frac{C_{Gmax}}{K_{65°C.} + V_g/V_l} = \frac{1,566}{1.26 + 0.25} = 1037 \; \mu mol/mol$$

The same fuel oil was then tested for hydrogen sulfide using conventional techniques first with GC-HS ATAE 29,90, (which is a standard laboratory liquid phase method for measuring total H₂S), and then with a Dräger Tube (which is a commonly used adsorbent tube with lead acetate which is sensitive to H₂S). The results are set forth below, in Table 2, and in comparison to the results obtained according to the multiple head space extraction system (MHES) of the present invention.

TABLE 2

| H₂S Concentration | MHES | GC-HS ATAE 29, 90 | Dräger Tube |
|---|---|---|---|
| $C_L°$ (μg/g) | 469.5 | >120 | >100 |
| $C_{Gmax}$ (μmol/mol) | 1566 | — | — |
| $C_{G65°C.}$ (μmol/mol) | 1037 | — | 800–1000 |

As indicated, the method of the present invention yields measurements of improved accuracy, and also provides information not available through conventional measurement techniques.

For example, the GC-HS ATAE 29,90 does not yield an equilibrium constant and, thus, no gas concentration in the vapor space was determined.

Next, in accordance with the invention, the equilibrium constant for any temperature, $K_{Ta}$, and thence the gas concentration $C_{GTa}$ were determined as follows.

Figure 8:
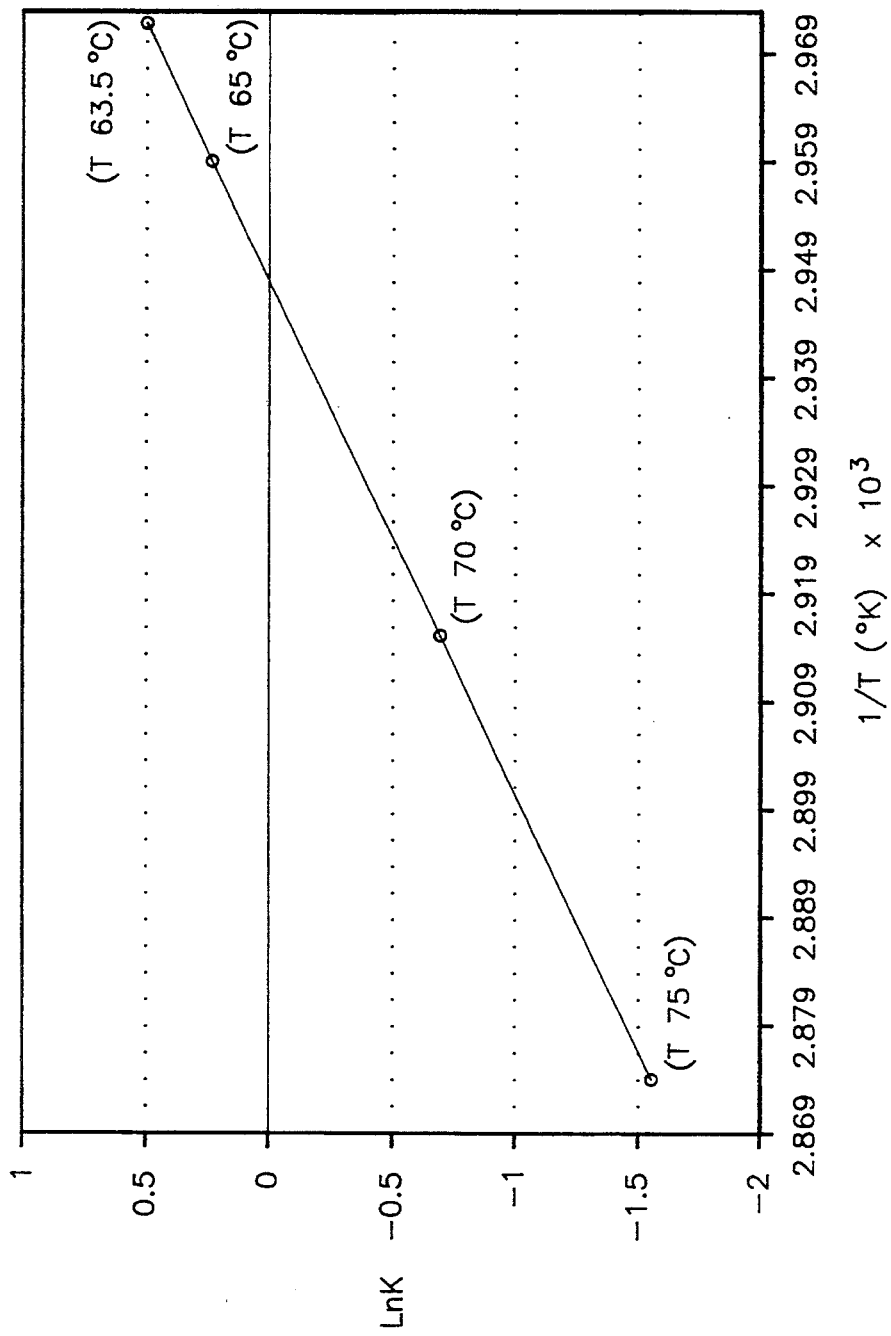
FIG. 8 is a graph illustrating the relationship between lnk and 1/T.

The equilibrium constant was determined for 70° C. ($K_{70°C.}$) following the same procedure used to obtain $K_{65°C.}$. $K_{70°C.}$ is 0.51. A graph of lnK v. 1/T was then prepared, as shown in FIG. 8. From the plots of $K_{65°C.}$, $K_{70°C.}$, a straight line relationship was drawn as shown. The equilibrium constant for 75° C. and also for 63.5° C. were then determined from the plot. Table 3 summarizes the values obtained.

TABLE 3

| T (°K.) | T (°C.) | K | lnK | 1/T (°K.) |
|---|---|---|---|---|
| 338 | 65 | 1.26 | 0.231 | 2.9586 × 10⁻³ |
| 343 | 70 | 0.51 | −0.673 | 2.9155 × 10⁻³ |
| 348 | 75 | 0.21 | −1.55 | 2.8736 × 10⁻³ |
| 336.5 | 63.5 | 1.66 | 0.51 | 2.9718 × 10⁻³ |

From these values, the actual gas concentration for 75° C. and 63.5° C. were estimated as follows:

$$C_{G75°C.} = \frac{C_{Gmax}}{K_{75°C.} + V_g/V_l} = 3404 \; \mu mol/mol$$

$$C_{G63.5°C.} = \frac{C_{Gmax}}{K_{63.5°C.} + V_g/V_l} = 820 \; \mu mol/mol.$$

Thus, according to the invention, the concentration of H₂S to be expected in the head space of a storage tank for a particular fuel oil was determined at numerous temperatures, and could be determined for any temperature, based upon minimal testing of a sample of the fuel oil.

It is to be understood that the invention is not limited to the illustrations described and shown herein, which are deemed to be merely illustrative of the best modes of carrying out the invention, and which are susceptible of modification of form, size, arrangement of parts and details of operation. The invention rather is intended to encompass all such modifications which are within its spirit and scope as defined by the claims.

What is claimed is:

1. A method for determining the maximum concentration of a monitored gas ($C_{Gmax}$) in the head space of a confined space containing a medium material, comprising the steps of:
   (a) providing extracting means having a chamber for receiving a sample volume of the material to be extracted from the confined space;
   (b) controlling the temperature of the chamber such that the temperature of the chamber is maintained at a desired temperature ($T_1$);
   (c) withdrawing a sample volume ($V_l$) of the material from the confined space and into the chamber;
   (d) feeding a volume ($V_g$) of inert gas into the chamber and mixing the inert gas with the material to form a mixture;
   (e) allowing the mixture to reach equilibrium wherein a head space of gas is formed in the chamber over the material;
   (f) withdrawing a first gas sample from the head space of the chamber;
   (g) determining the concentration ($C_{g1}$) of the monitored gas in the first gas sample;
   (h) expelling the head space gas from the head space of the chamber;
   (i) repeating steps (d)–(g) so as to determine the concentration ($C_{gn}$) of the monitored gas in at least a second gas sample;
   (j) determining the equilibrium constant ($K_{T1}$) of the material at the given temperature ($T_1$) in accordance with the following formula:

$$K_{T1} = \frac{V_g/V_l(e^x)}{1 - e^x}$$

wherein:

$$x = \frac{\ln C_{gn} - \ln C_{g1}}{n - 1}$$

and wherein:
   n = the sequential number of the sample taken and is greater than 1;
   (k) determining the maximum concentration ($C_{Gmax}$) of the monitored gas in the head space of the confined space in accordance with the following formula:

$$C_{Gmax} = C_{g1} \cdot (K_{T1} + V_g/V_l) \cdot D_f$$

where $D_f$ is a dilution factor defined as follows:

$$D_f = \frac{V_g \cdot Wt_t}{Wt_s \cdot V_{ts}}$$

wherein:
- $Wt_s$ is the weight of the sample volume ($V_l$) of the material;
- $Wt_t$ is the total weight of the medium material;
- $V_{vs}$ is the volume of the head space of the confined space; and
- $V_g$ is the volume of inert gas.

2. A method according to claim 1, wherein the given temperature ($T_1$) is the temperature of the medium in the confined space.

3. A method according to claim 1, further including the step of determining the actual concentration ($C_G$) of the monitored gas in the head space as follows:

$$C_G = \frac{C_{Gmax}}{K_{T1} + V_g/V_l}.$$

4. A method according to claim 1, further comprising the steps of:
   (a) repeating steps (b)–(j) of claim 1 at a temperature ($T_2$) for calculating the equilibrium constant ($K_{T2}$) of the material at the temperature ($T_2$);
   (b) plotting a graph of lnK vs. 1/T for the values ($K_{T2}$), ($K_{T1}$), ($T_2$), and ($T_1$); and
   (c) determining from the graph the equilibrium constant ($K_{Ta}$) of the material at any temperature ($T_a$).

5. A method according to claim 4, further comprising the step of determining the actual concentration ($C_{GTa}$) of the monitored gas at any temperature ($T_a$) as follows:

$$C_{GTa} = \frac{C_{Gmax}}{K_{Ta} + V_g/V_l}.$$

6. A method for determining the equilibrium constant ($K_{Ta}$) between the liquid phase and gas phase of a medium material contained in a confined space at a temperature ($T_a$) comprising the steps of:
   (a) providing extracting means having a chamber for receiving a sample volume of the material to be extracted from the confined space;
   (b) maintaining the temperature of the chamber at a temperature ($T_1$);
   (c) withdrawing a sample volume ($V_l$) of the material from the confined space and into the chamber;
   (d) feeding a volume ($V_g$) of inert gas into the chamber and mixing the inert, gas; with the material to form a mixture;
   (e) allowing the mixture to reach equilibrium wherein a head space of a gas is formed in the chamber over the material;
   (f) withdrawing a first gas sample from the head space of the chamber;
   (g) determining the concentration ($C_{gl}$) of the monitored gas in the first gas sample;
   (h) expelling the head space gas from the head space of the chamber;
   (i) repeating steps (d)–(g) so as to determine the concentration ($C_{gn}$) of the monitored gas in at least a second gas sample;
   (j) determining the equilibrium constant ($K_{T1}$) of the material at the temperature ($T_1$) in accordance with the following formula:

$$K_{T1} = \frac{V_g/V_l(e^x)}{1 - e^x}$$

wherein:

$$x = \frac{\ln C_{gn} - \ln C_{gl}}{n - 1}$$

and wherein:
- n = the sequential number of the sample taken and is greater than 1;
   (k) repeating steps (c)–(j) at a temperature ($T_2$) for calculating the equilibrium constant ($K_{T2}$) of the material at the temperature ($T_2$);
   (l) plotting a graph of lnk vs. 1/T for the values ($K_{T2}$), ($K_{T1}$), ($T_2$), and ($T_1$); and
   (m) determining from the graph the equilibrium constant ($K_{Ta}$) of the material at any temperature ($T_a$).

7. A method for determining the total concentration of a monitored gas ($C_L°$) in a medium material, comprising the steps of:
   (a) providing extracting means having a chamber for receiving a sample volume of the material to be extracted from the confined space;
   (b) controlling the temperature of the chamber such that the temperature of the chamber is maintained at a desired temperature ($T_1$);
   (c) withdrawing a sample volume ($V_l$) of the material from the confined space and into the chamber;
   (d) feeding a volume ($V_g$) of inert gas into the chamber and mixing the inert gas with the material to form a mixture;
   (e) allowing the mixture to reach equilibrium wherein a head space of gas is formed in the chamber over the material;
   (f) withdrawing a first gas sample from the head space of the chamber;
   (g) determining the concentration ($C_{gl}$) of the monitored gas in the first gas sample;
   (h) expelling the head space gas from the head space of the chamber;
   (i) repeating steps (d)–(g) so as to determine the concentration ($C_{gn}$) of the monitored gas in at least a second gas sample;
   (j) determining the equilibrium constant ($K_{T1}$) of the material at the given temperature ($T_1$) in accordance with the following formula:

$$K_{T1} = \frac{V_g/V_l(e^x)}{1 - e^x}$$

wherein:

$$x = \frac{\ln C_{gn} - \ln C_{gl}}{n - 1}$$

and wherein:
- n = the sequential number of the sample taken and is greater than 1;
   (k) determining the total concentration ($C_L°$) of the monitored gas in the medium in accordance with the following formula:

$$C_L° = C_{gl} \cdot (K_{T1} + V_g/V_l).$$

* * * * *